(12) United States Patent
Wittkampf et al.

(10) Patent No.: US 7,998,141 B2
(45) Date of Patent: *Aug. 16, 2011

(54) IRRIGATED CATHETER AND METHOD, IN PARTICULAR FOR ABLATION AND LIKE TECHNIQUES

(75) Inventors: Frederik Henricus Wittkampf, Bilthoven (NL); Hiroshi Nakagawa, Edmond, OK (US)

(73) Assignees: University Medical Center Utrecht (NL); University of Oklahoma, Norman, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/900,983

(22) Filed: Oct. 8, 2010

(65) Prior Publication Data

US 2011/0022046 A1 Jan. 27, 2011

Related U.S. Application Data

(63) Continuation of application No. 10/595,608, filed as application No. PCT/NL2004/000741 on Oct. 20, 2004, now Pat. No. 7,815,635.

(30) Foreign Application Priority Data

Oct. 29, 2003 (NL) .................................. 1024658

(51) Int. Cl.
*A61B 18/18* (2006.01)
(52) U.S. Cl. ............... 606/41; 606/39; 606/49; 607/116
(58) Field of Classification Search .............. 606/20–52; 607/99–101
See application file for complete search history.

(56) References Cited

U.S. PATENT DOCUMENTS

| 5,098,431 | A | 3/1992 | Rydell |
| 5,843,152 | A * | 12/1998 | Tu et al. ..................... 607/122 |
| 6,017,338 | A | 1/2000 | Brucker et al. |
| 6,049,737 | A | 4/2000 | Simpson et al. |
| 6,123,703 | A | 9/2000 | Tu et al. |
| 6,171,275 | B1 | 1/2001 | Webster, Jr. |
| 6,500,175 | B1 | 12/2002 | Gough et al. |
| 6,611,699 | B2 | 8/2003 | Messing |
| 6,662,034 | B2 | 12/2003 | Segner et al. |
| 7,150,744 | B2 | 12/2006 | Edwards et al. |
| 7,311,708 | B2 | 12/2007 | McClurken |
| 2002/0087156 | A1 | 7/2002 | Maquire et al. |
| 2002/0156470 | A1 | 10/2002 | Shadduck |

FOREIGN PATENT DOCUMENTS

| EP | 0856292 | 8/1998 |
| WO | WO-9636860 | 11/1996 |

OTHER PUBLICATIONS

Wittkampf, Fred H. , "Radiofrequency ablation with a cooled porous electrode catheter", *JACC* vol. II, No. 2 Feb. 1988; 17a.

* cited by examiner

*Primary Examiner* — Linda Dvorak
*Assistant Examiner* — Amanda Scott

(57) ABSTRACT

The invention relates to a variety of catheters provided with an elongate body with an electrically conductive first end. Wherein through said elongate body at least one conductive wire extends which is connected to an electrode. The electrode is coupled to said first end and an irrigation means (e.g. a channel, duct, tube, etc.) for feeding an irrigation fluid through said elongate body, where said irrigation means is provided, in, on, near, through, or adjacent said first end with at least one outlet opening, while said irrigation means is at least partially thermally insulated from said first end. Optionally a temperature sensor couples to the first end.

19 Claims, 3 Drawing Sheets

IRRIGATED CATHETER AND METHOD, IN PARTICULAR FOR ABLATION AND LIKE TECHNIQUES

CROSS-REFERENCE TO RELATED APPLICATIONS

This application is a continuation of copending U.S. application Ser. No. 10/595,608 (filed Apr. 5, 2007), scheduled to issue as U.S. Pat. No. 7,815,635 on 19 Oct. 2010, which is a national stage filing based upon international application no. PCT/NL2004/000741, filed 20 Oct. 2004 and published in English on 2 Jun. 2005 under international publication no. WO 2005/048858 (the '741 application), which claims priority to Dutch application no. 1024658, filed 29 Oct. 2003 (the '658 application). The '741 application, the '658 application, and the '608 application are all hereby incorporated by reference as though fully set forth herein.

BACKGROUND OF THE INVENTION a. Field of the Invention

The invention relates to a variety of catheters. The invention relates in particular to irrigated catheters for ablation in body cavities such as blood vessels or organs such as a heart.

b. Background Art

It is known to perform treatments in a human or animal body with the aid of catheters having an electrically conductive first end. This ablation electrode is typically present on the end of the catheter. There are also embodiments with several ablation electrodes one behind the other on the catheter which is inserted into said cavity. The patient is then laid on a conductive plate, for instance a grounding plate. Then, an electric current is passed through the catheter, which current flows through the body. If the first end is held against or at a very short distance from a wall of the body cavity, said wall will be heated locally over a relatively small area as a result of the electrical resistance of the wall. Consequently, ablation occurs in said area. As a result thereof, part of the tissue of said wall dies. With this treatment, for instance cardiac arrhythmias can be treated and prevented in the future.

During this known treatment, it is of importance that the temperature of, in particular, said first end of the catheter can be controlled in order to evaluate the amount of warming of the target area; hence, based on inter alia this temperature, the power which is to be supplied to this first end can be controlled. Moreover, prior to the actual treatment, with the aid of a relatively small amount of power, the abutment of said first end against the wall can be assessed based on the temperature increase which is measured in said first end. In fact, a poorer abutment will lead to a smaller temperature increase when the power supplied remains the same. Moreover, the temperature in the fluid, in particular blood, is to be prevented from rising too much around said first end because clogging can occur as a result thereof, which clogging can lead to dangerous situations in the body. Moreover, too strong a heating of the first end of the catheter can lead to blistering, explosions due to boiling of entrapped liquid in the wall of the respective cavity such as the heart, which is dangerous to the health and, in extreme cases, can lead to openings in the heart wall. Furthermore, the danger exists that undesirably large areas are affected, as a result of which damage to, for instance, an AV-node can occur. In order to be able to measure this temperature, it is known to include a temperature sensor such as a thermocouple in said first end.

In order to prevent said first end of the catheter from being heated too strongly, it has been proposed to cool this first end.

To that end, Wittkampf (Journal of the American College of Cardiology 1988, 11, p. 17A) has described a catheter wherein a fluid channel is provided in the catheter, which channel terminates in outlet openings in said first end. A cooling medium such as physiological saline solution can be forced through said channel and provides continuous cooling of said first end during use. Thus, the temperature thereof can be kept low. However, a disadvantage of this known catheter is that the actual temperature of said first end cannot be accurately measured.

In order to solve this disadvantage, it has already been proposed to also include a thermocouple in said first end in such a catheter. However, as a result of said cooling, this temperature reading is inaccurate. Consequently, the temperature change of said end and, hence, of for instance the fluid, in particular the blood around said first end or the temperature of the wall, cannot be verified sufficiently accurately, so that clots can still occur. Moreover, the extent of the temperature increase of the wall cannot be sufficiently controlled and verified. Because the first end of this catheter remains relatively cool, no deposits of such clots will be detected on said exterior, which entails the risk that it can be wrongfully assumed that no clots have formed during the treatment. In fact, the fluid, in particular the blood around said first end and/or the wall, may very well have been heated such that coagulation has occurred, resulting in clots.

In an alternative known embodiment, a catheter is provided with a closed channel extending through said first end, with which the first end is cooled from the inside. Here, the same dangers arise as with the above-described catheter. Moreover, the great drawback is that the blood is not cooled at all.

BRIEF SUMMARY OF THE INVENTION

The invention aims to provide a catheter with which treatments that require local heating of a body cavity wall, such as ablation, can be performed in a safe and accurate manner.

The invention furthermore aims to provide such a catheter with which abutment of a first end thereof against a wall can be assessed during use in a simple and accurate manner.

A further object of the invention is to provide a catheter with which, the first, leading end can be heated during use in a simple and accurate manner, in particular with the aid of current, whereby clots can be prevented in a simple manner.

The invention further aims to provide a catheter which is compatible with existing devices for ablation techniques.

A number of these and other objects are achieved with a catheter according to the invention.

With a catheter according to the invention, an elongated body is provided, through which a current-carrying wire extends, coupled to an electrically-conductive first end. Moreover, a channel extends through said elongated body and terminates in or near a leading first end in at least one outlet opening. During use, fluid can be guided through said channel, which fluid can flow out of said at least one outlet opening. In or near said first end, a temperature sensor has been arranged, with which the temperature of said first end can be measured during use.

With a catheter according to the invention, a thermal separation is provided between the channel and the electrode. This thermal separation is provided such that fluid flowing through the channel during use substantially does not come into contact with the electrode before it flows out of at least one first outflow opening. Thus, during use, it is ensured that it is not the electrode that is cooled by said fluid, at least not directly, but rather the fluid extending therearound, in particular blood.

With this, coagulation can be prevented while the temperature of the electrode can be accurately measured.

In an advantageous embodiment, a catheter according to the invention is further characterized in that said channel has a longitudinal direction and is provided with a series of outlet openings, which outlet openings are positioned such that cooling medium supplied, during use, through said channel flows through said outlet openings in an outflow direction, which forms an angle with said longitudinal direction. This angle is for instance between 30° and 90°, more particularly between 45° and 90°, so that the outflow direction is directed substantially away from the outside of the first end. Furthermore, an outlet opening can also be provided in the axially leading end of said first end.

In an alternative embodiment, one or more outlet openings can be provided in a leading longitudinal edge of said body, such that during use, a flow is obtained substantially along the outside surface of said first end. To that end, the respective at least one outlet opening can be located adjacent said first end, when viewed in front view. An advantage of such an embodiment can be, for instance, a simple construction, no channel extending through the respective first end and/or an advantageous outflow pattern.

In an advantageous embodiment, the or each outlet opening is implemented such that a somewhat turbulent flow is created around said first end, so that coagulation is prevented even better.

In a practical embodiment, at least in and/or adjacent the first end, the channel and/or the outlet openings are provided with a thermally-insulating inner casing and/or are formed in a thermally poorly-conductive material. Herein, thermally poorly-conductive is understood to at least include heat transfer across the wall of the channel to the first end which is considerably less, for instance 10% or more, more particularly 25% or more, than the heat transfer across the wall of a channel which would occur with a similar catheter of similar dimensions, but without such thermally-insulating features.

The temperature sensor, which can for instance be implemented in a known manner as a thermocouple, is preferably incorporated in the first end, at a distance from the interface between said first end and the body of the catheter, preferably adjacent the middle of the electrode. As a result, an accurate temperature measurement of said first end becomes possible. With automatically performed treatments, this sensor can also be used as a switch.

The first end can be manufactured from a thermally and electrically conductive material such as metal. Also, only an outer casing can be provided with metal, on, for instance, a plastic, ceramic or glass core, whereby already a part of the desired thermal insulation can be obtained.

The invention further relates to a method for thermal treatment such as ablation.

With such a method, the temperature of a first end of an ablation catheter can be more accurately checked and controlled, so that ablations and other thermal treatments can be accurately and safely performed in body cavities such as blood vessels, a heart and the like. With a method according to the invention, the temperature of a wall part of a body cavity can be especially accurately controlled, without the danger arising that coagulation occurs in blood flowing around said wall part. Coagulation of proteins in blood can lead to clot formation, which clots can become dislodged in the blood flow and can lead, for instance, to infarcts. Clots are to be avoided, in particular, in the left ventricle and atrium of the heart. With a method according to the invention, the temperature of the blood around said wall part is preferably kept below the coagulation temperature, while the tip of the employed catheter and/or the to-be-treated wall part can be heated to the desired, possibly higher, temperature. The or each electrode is thereby heated substantially by the adjacent wall, wherein a temperature increase occurs as a result of resistance. The extent of contact between the wall and the electrode will therefore influence the heating of the electrode. This is a reason why a contact measurement can be important.

With this method, a cooling fluid such as a physiological saline solution is supplied, preferably in a known manner, through a channel extending through the catheter, which cooling fluid is directly introduced into the respective body cavity. In a method according to the invention, said cooling fluid is preferably thermally insulated to a high extent from the material of the leading first end of the catheter during use, so that the blood around this first end is cooled more intensively than the first end itself Preferably, the temperature of the first end is measured accurately thereby, the temperature of the wall, against which or at which the catheter is held can be accurately controlled.

With the aid of said cooling fluid, the temperature of the blood around said first end is preferably kept lower than approximately 55° C. The temperature of the outside of the first end is thereby preferably kept below approximately 65° C.

With the aid of the cooling fluid, turbulence is preferably generated in the blood around said first end, whereby clot formation in the blood is prevented even better.

In the further subclaims, further advantageous embodiments of the invention are described. For explanation of the invention, embodiments of the invention will be further described with reference to the drawings.

DETAILED DESCRIPTION OF EMBODIMENTS OF THE INVENTION

Figure 1:
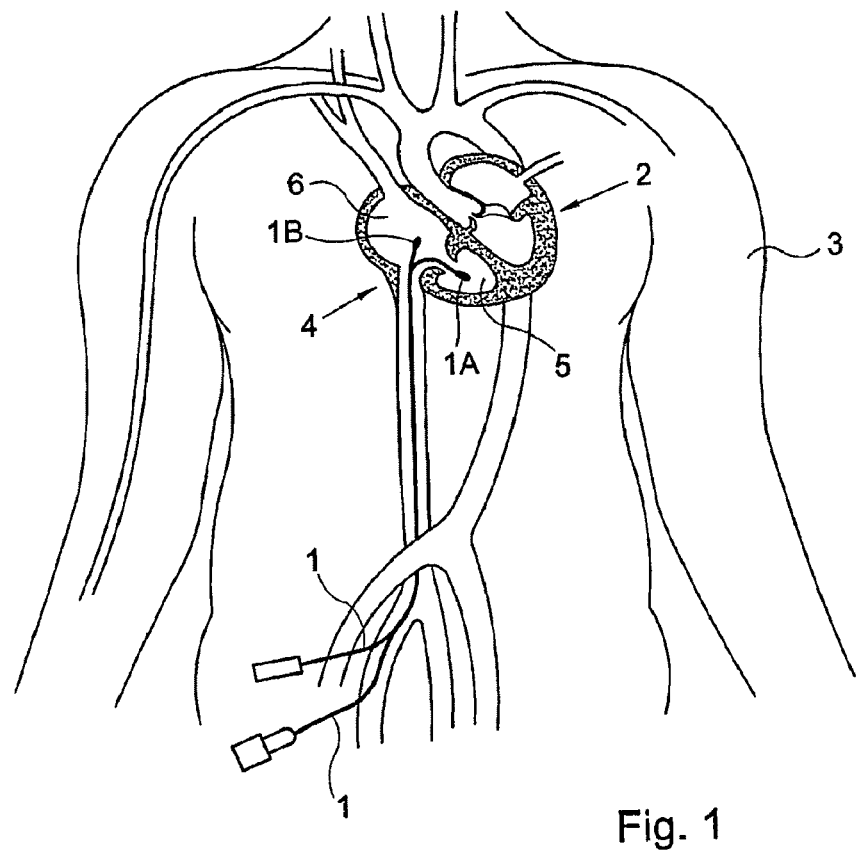
FIG. 1 schematically shows a catheter according to the invention with a first end in a heart ventricle.

In this description, identical or corresponding parts have identical or corresponding reference numerals. The depicted embodiments are given only by way of example and should not be construed as being limitative in any manner. In particular, combinations of parts of the embodiments shown are also understood to be described herein. A body cavity is understood herein to include at least each part of a human or animal body which can be reached by a forward end of a catheter.

In FIG. 1 it is schematically shown how a catheter 1 has been inserted into a heart 2 of a patient 3. A forward end 4 of a catheter 1A is inserted into a ventricle 5, in particular a right ventricle of the heart, while the corresponding forward end 4 of a second catheter 1B is inserted into the right atrium 6 of the heart 2. This is merely shown as an illustration of possible positions. The catheter(s) is or are inserted into the heart 2 from, for instance, the groin of the patient 3, which is a known method and will therefore not be described further; the known method and device for controlling these catheters and the mechanisms thereto in the catheter also will not be described.

Figure 2:
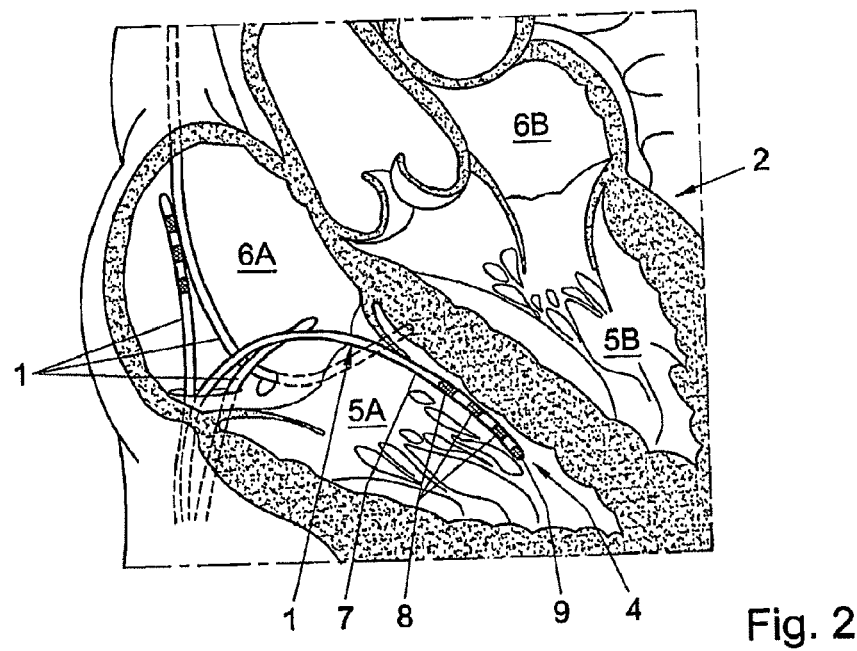
FIG. 2 schematically shows a number of catheters in a heart, for a treatment of cardiac arrhythmias.

In FIG. 2, a heart 2 is shown in cross section with left and right ventricle 5A, 5B and left and right atrium 6A, 6B. Four catheters 1 have been inserted into this heart 2. During, for instance, a measurement and/or treatment of cardiac arrhythmias, one or more catheters 1 can be inserted into the heart 2, in order to obtain a clear picture of the electric currents in the heart. Each of the depicted catheters 1 has a body 7 which is elongated and can be guided through the vascular system of the patient. The body 7 has a forward end 4, hereinafter called the first end 4, which is inserted into the heart 2. In, or at least adjacent the first end, a number of electrodes 8 are provided in the form of metal rings, for instance three, which are separated from each other by electrically insulating material of the body and each can be connected with electronic equipment via a conductive wire through the body 7, so that measurements can be carried out in a known manner, for instance an electrogram can be made.

The first end 4 is further provided with a tip 9 manufactured from an electrically conductive material such as metal, which tip can be connected via an electrically-conductive wire 10 (FIGS. 3-4) with said electronic equipment (not shown), with which current can be fed via the wire 10 into said tip 9. During the measurement and/or the treatment, the patient lies on an electrically conductive sub-surface, for instance on a grounding plate (not shown). For performing the treatment, for instance an ablation, the tip 9 of the catheter 1 is pressed against the wall 11 of the heart 2, so that a current will start to flow through said wall 11. As a result of electrical resistance of the tissue of the wall, heat development will occur adjacent the tip 9, whereby tissue can be treated, in particular heart muscle cells can be killed, so that undesired conduction pathways in the heart 2 or undesired sources of arrhythmias can be blocked. This is a known treatment, called ablation technique, for preventing cardiac arrhythmias. For a further description of these techniques, reference is made to the publications and relevant manuals mentioned in the introduction.

Figure 4:
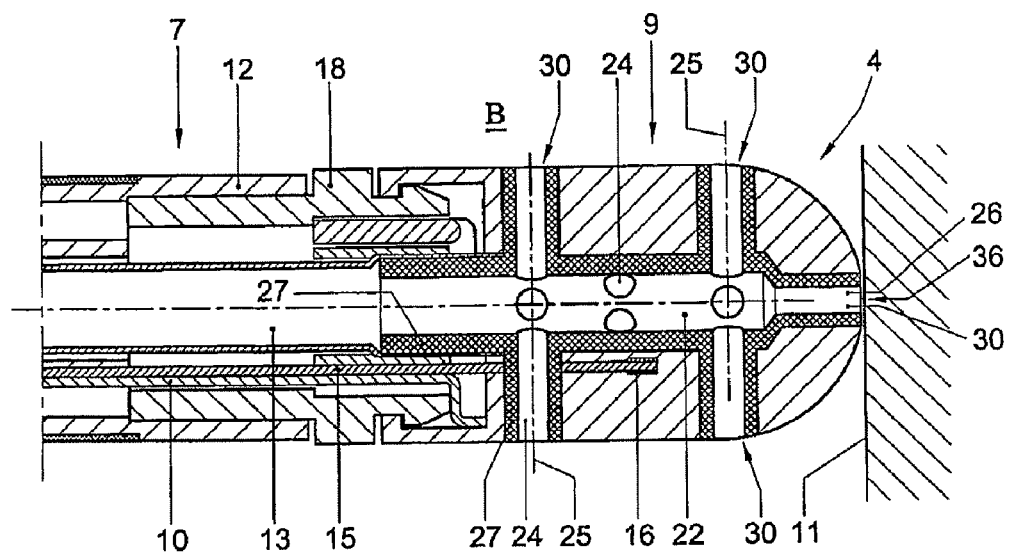
FIG. 4 schematically shows, greatly enlarged, in cross section, a forward end of a catheter according to the invention, in a second embodiment.
Figure 5:
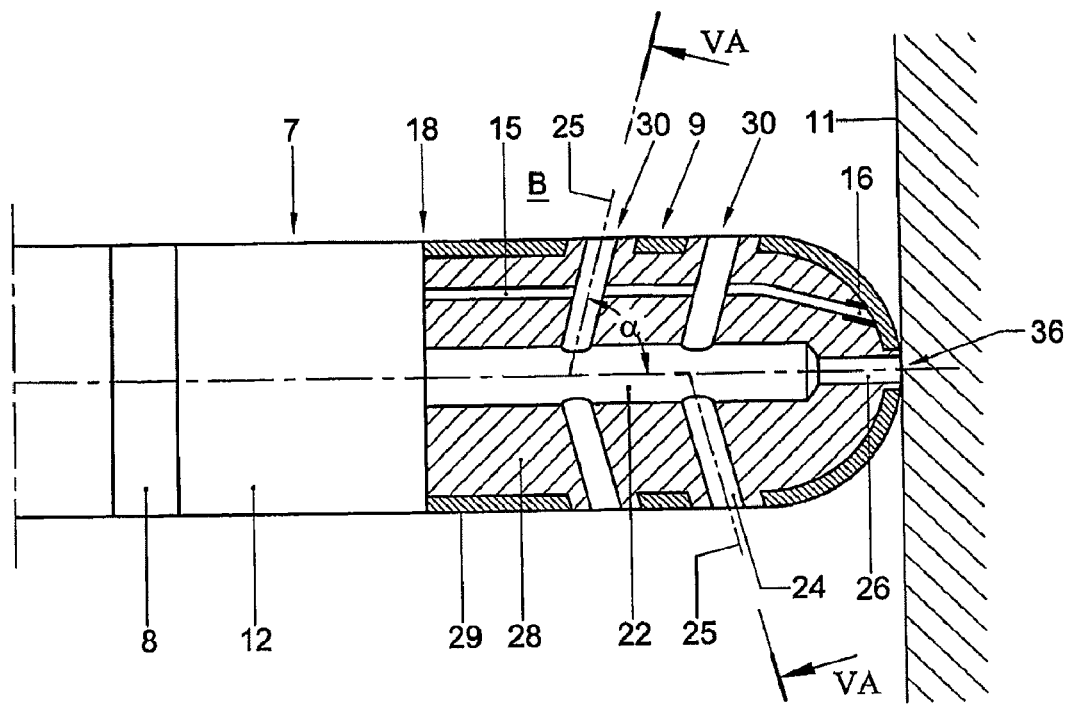
FIG. 5 schematically shows, greatly enlarged, in cross section, a forward end of a catheter according to the invention, in a third embodiment.

It is known to use a cooling fluid in a catheter 1 for use in, for instance, ablation techniques. This is brought through a channel in the catheter to the forward end of the catheter and from there, it is either introduced into the blood stream or returned through the catheter. The cooling fluid is thereby brought against the inside of the catheter into close contact with the to-be-cooled electrode, such as the tip of the catheter, in order to cool this electrode and thereby prevent deposition of proteins on the outside. Such a catheter is, for instance, described in EP 0 856 292. However, such catheters have the disadvantage that the temperature of the respective electrode, such as the tip, no longer offers a good representation of the heat development in said wall 11 and/or in the blood B, as seen in FIGS. 3-5, around said electrode.

With a catheter 1 according to the invention, these disadvantages have been solved in that, during use, said electrode such as the tip 9 is not cooled, at least not directly, but rather the blood B is, so that no coagulation occurs and clots are prevented. As a result, the temperature of the respective electrode, such as the tip 9, can be accurately measured and controlled, while an estimate of the temperature of the wall 11 can be accurately made from it.

Hereinafter, a number of examples of catheters 1 according to the invention will be described.

Figure 3:
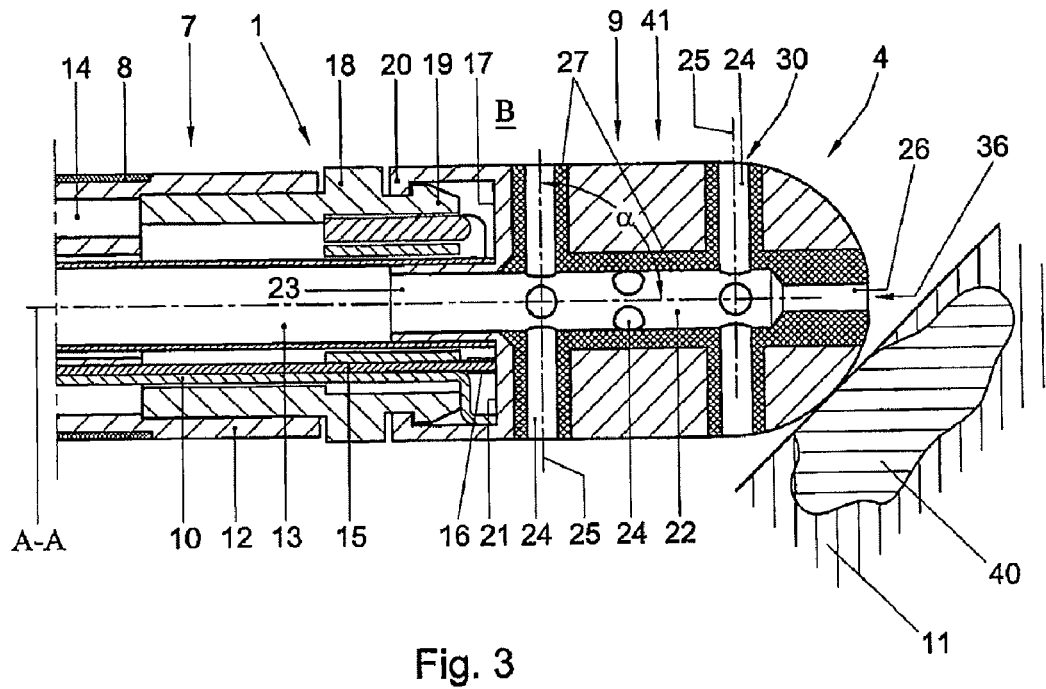
FIG. 3 schematically shows, greatly enlarged, in cross section, a forward end of a catheter according to the invention, in a first embodiment.

In FIG. 3, a first embodiment of a forward end of a catheter 1 according to the invention is shown, in cross-sectional side view.

This catheter 1 comprises an elongated body 7 with a first end 4, formed by a tip 9 made of an electrically and thermally conductive material, in particular metal such as platinum. The body has a longitudinal axis A-A and comprises a substantially cylindrical wall 12 through which a channel 13 extends. Between the wall 12 and the channel 13, there is an annular space 14 through which extends, for instance, the electrically conductive wire 10, the different connecting points for the electrodes 8 and known control means (not shown) for controlling the end 4. Moreover, a second electrically-conductive wire 15 extends through the annular space 14, which wire 15 is connected to a thermocouple 16.

In the embodiment shown in FIG. 3, the tip 9 is coupled to the body 7 by means of a coupling part 18 which is attached, for instance glued, to a first side inside the wall 12, and, on the other side, is fitted in a compatible second snap edge 20 of the tip 9 via a snap edge 19. In this embodiment, the thermocouple 16 is arranged in or against the interface 17 between the body 7 and the tip 9, at least on the end surface 21 of the tip 9 proximal to the body 7 and the coupling part 18.

In the first end 4, in particular in the tip 9, a channel part 22 is provided extending in line with the axis A-A and is connected to the channel 13, for instance because a sleeve 23 extends from said end surface 21 in the channel 13 and is fitted therein. From an exterior 41 of the tip 9, first bores 24 are provided reaching into the channel part 22 and extending substantially radially. These first bores 24 all have a longitudinal axis 25 forming an angle α with the longitudinal axis A-A of the body 7, for instance approximately 90°. A second bore 26 is provided in line with the channel 13, at least with the axis A-A, which bore 26 terminates in the apex 36 of the tip 9. In each bore 24,26, as well as around the channel part 22, a thermal insulating casing 27 is provided, such that during use a cooling fluid, in particular a physiological saline solution, can be passed through the channel 13, the channel part 22 and the bores 24,26 without direct contact occurring between the cooling fluid and (the inside of) the tip 9. Direct cooling of the tip 9 by the cooling fluid is thereby prevented in large part. In the embodiment of FIG. 3, the sleeve 23 is not thermally insulated.

In FIG. 4, a first, more advantageous alternative embodiment of a first end 4 of a catheter 1 according to the invention is shown, distinguished from the one according to FIG. 3 in that herein, the sleeve 23 is also thermally insulated, while the thermocouple 16 is also arranged closer to the apex 36 of the tip 9, whereby an even more accurate temperature measurement of, in particular, the heart wall can be performed.

Figure 5A:
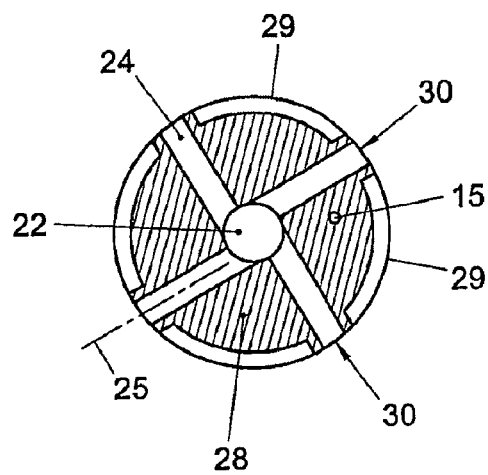
FIG. 5A shows a cross section along the line VA-VA in FIG. 5.

In FIGS. 5 and 5A, a further alternative embodiment is shown, with only tip 9 shown in cross-section, which largely corresponds in a constructional sense to the embodiments of FIGS. 3 and 4. However, a tip 9 is provided herein that has a core 28, which is manufactured from a material having a low thermal and/or electrical conductivity, for instance glass, ceramics or plastic, and a casing 29 having good heat conductivity and/or electrical conductivity relative thereto. Herein, the bores 24,26 have been provided with a thermal inner casing from the casing 29, at least being formed as part of the core 28, whereby the desired thermal insulation is obtained in a simple manner. In this embodiment, the longitudinal axes 25 extend approximately tangentially relative to the channel part 22 (FIG. 5A) and form an angle α with the longitudinal axis A-A, which angle deviates from 90°, for instance approximately 75° to 80°, such that the outflow direction is somewhat in the direction of the apex 36, at least in the direction of the wall 11. Thereby, the cooling of the blood around the tip 9 and adjacent the wall 11 can be improved even more. A thermocouple 16 is attached to the casing 29.

In the embodiments according to the FIGS. 3-5, the end of each bore 24,26 always form an outflow opening 30 for cooling fluid. These outflow openings 30 can for instance be formed such that during use a turbulent flow is generated in the blood flowing by. Means that can be used therefore are known from fluid dynamics. For instance, thirteen outflow openings are provided in the depicted embodiments, but it will be clear that any desired number of outflow openings 30 can be provided.

Optionally, one or more outlet openings can be provided near the electrode, in particular near the interface 17 between the body 7 and the tip 9, so that a part of the cooling fluid is directed along the tip 9, at least along the outer surface of the electrode, for direct cooling of the blood and/or for generating turbulence.

When using a catheter 1 according to the invention in a treatment of, for instance, cardiac arrhythmias or the like, wherein an ablation technique is used in a body cavity, in which blood is flowing through, such as a ventricle or atrium of a heart or an artery or a vein, the current intensity and the supply of cooling fluid are preferably regulated such that the temperature of the blood around the tip 9 is kept below the coagulation temperature. In practice, this means below approximately 55° C., so that no coagulation occurs. Preferably, the temperature of the tip 9 is regulated such that it does not exceed 65° C. In practice, this has appeared to be a reasonably safe limit. With larger electrodes (of a length of, for instance, 8 mm instead of 4 mm), the flowing blood will provide proportionally more cooling so that there is a greater difference between the tissue and electrode temperature. With an 8 mm tip, 50 to 55° C. is a good target value, at least with existing electrodes. The electrode will clearly remain cooler than the heated tissue of the wall, which is kept below 100° C. in order to prevent the earlier-mentioned explosions. In FIG. 3, an area 40 is schematically indicated in the wall 11 wherein heat development occurs as a result of the current passed through the wall 11, as described earlier. Naturally, as to dimension and shape, this influenced area 40 depends on the current intensity used and the duration of the treatment and is only given as an indication.

The invention is not limited in any manner to the exemplary embodiments given in the description and the drawing. Many variations thereon are possible within the framework of the invention as outlined by the claims.

For instance, different materials can be used for the different parts, and outflow openings can be provided in different manners, as long as the tip 9 is at least substantially prevented from being cooled from the inside by cooling fluid flowing therethrough. The leading end of the catheter can have any desired shape and can also be used at different locations than in the heart, for instance also for fighting tumors and such aberrations or for targeted creation of scar tissue. A catheter according to the invention can also be provided with several electrodes, at least one of which being provided with a cooling device according to the invention, with insulated outflow openings. Also, only one electrode can be provided at a distance from the end.

These and many comparable variations are understood to fall within the framework of the invention as outlined by the claims.

We claim:

1. A catheter comprising:
   an elongate body having a longitudinal axis;
   an electrode coupled to a distal end portion of the elongate body;
   a conductive wire extending through said elongate body and electrically coupled to said electrode;
   an irrigation channel or an irrigation tube extending through said elongate body and having a distal end; and
   at least one outlet opening extending radially from the longitudinal axis, and fluidly coupled to, the distal end of the irrigation channel or the irrigation tube;
   wherein said at least one outlet opening includes one of a thermally insulating interior casing and a thermally insulating interior material,
   wherein a distal end of the outlet opening terminates adjacent the electrode.

2. A catheter according to claim 1, wherein said at least one outlet opening couples to a lateral exterior portion of the elongate body.

3. A catheter according to claim 1, wherein the at least one outlet opening couples to the longitudinal axis of said irrigation channel or said irrigation tube at an angle of between about 30 degrees and about 90 degrees.

4. A catheter according to claim 1, wherein the electrode comprises:
   a core manufactured from a material having one of a low thermal conductivity characteristic and a low electrical conductivity characteristic; and
   an outer casing surrounding at least a substantial interior portion of the core;
   wherein said casing comprises a material having one of a higher heat conductivity and a higher electrical conductivity relative to the core material.

5. A catheter according to claim 4, wherein the core comprises at least one of a plastic material, a ceramic material, and a glass material, and wherein the outer casing comprises a metallic material.

6. A catheter according to claim 5, wherein the metallic material comprises at least a portion of a platinum material.

7. A catheter according to claim 5, further comprising a temperature sensor coupled to said electrode.

8. A catheter according to claim 7, wherein the temperature sensor comprises a thermocouple coupled to a portion of the outer casing.

9. A catheter according to claim 7, wherein the temperature sensor comprises at least one of a thermocouple and a thermistor.

10. A catheter according to claim 1, further comprising a temperature sensor coupled to said electrode.

11. A catheter comprising:
    an elongate body having a longitudinal axis;
    an electrode coupled at a distal end portion of the elongate body;
    a conductive wire extending through said elongate body and electrically coupled to said electrode;
    an irrigation duct extending through said elongate body; and
    at least one outlet opening, having a first end and a second end, extending radially from a distal end of the irrigation duct;
    wherein said first end is fluidly coupled to a distal end of the irrigation duct;
    wherein said second end terminates near the electrode;
    wherein the at least one outlet opening includes a thermally insulating material coupled to a portion of an interior casing disposed in the irrigation duct.

12. A catheter according to claim 11, wherein said irrigation channel or said irrigation duct is configured to couple a fluid from a remote source of fluid through said elongate body and egress from said at least one outlet opening.

13. A catheter according to claim 12, wherein said at least one outlet opening is adapted to deliver said fluid to an outer surface of said elongate body in an outflow direction, and wherein said outflow direction comprises an angle relative to said longitudinal axis.

14. A catheter according to claim 11, further comprising a temperature sensor coupled to a portion of the electrode.

15. A catheter according to claim 11, wherein said second end couples to an outer portion of the elongate body.

16. A method, comprising:
    deploying a catheter having a longitudinal axis and an electrode coupled to a distal end portion thereof, into contact with a volume of a target tissue, wherein said catheter includes an irrigation channel or an irrigation tube extending through said elongate body and at least one outlet opening fluidly coupled to and extending radially from the irrigation channel or tube, wherein at least an interior portion of the outlet opening comprises a thermally insulating casing;
    at least one of dispensing fluid or not dispensing fluid from a remote vessel through the irrigation channel or tube and the outlet opening and into contact with the volume of target tissue; and
    measuring a temperature of said electrode with a temperature sensor coupled to the electrode and thermally insulated and spaced from the irrigation channel or tube and the outlet opening.

17. A method according to claim 16, wherein the thermally insulating casing further comprises an electrically insulative material.

18. A method according to claim 17, wherein one of the thermally insulating casing and the electrically insulative material comprises a preformed tubular member.

19. A method according to claim 16, wherein the measuring step comprises measuring said electrode during at least one of dispensing fluid and not dispensing fluid.

* * * * *